(12) United States Patent
Urakawa et al.

(10) Patent No.: US 8,242,217 B2
(45) Date of Patent: Aug. 14, 2012

(54) EPOXY RESIN CURING AGENT, PROCESS FOR PREPARING THE SAME, AND EPOXY RESIN COMPOSITION

(75) Inventors: Yoshifumi Urakawa, Minato-ku (JP); Hideo Miyata, Minato-ku (JP); Isao Yamagami, Minato-ku (JP); Katsumi Murofushi, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 68 days.

(21) Appl. No.: 12/747,556

(22) PCT Filed: Dec. 8, 2008

(86) PCT No.: PCT/JP2008/072266
§ 371 (c)(1),
(2), (4) Date: Jun. 11, 2010

(87) PCT Pub. No.: WO2009/075252
PCT Pub. Date: Jun. 18, 2009

(65) Prior Publication Data
US 2010/0273940 A1 Oct. 28, 2010

(30) Foreign Application Priority Data

Dec. 13, 2007 (JP) .................................. 2007-322329

(51) Int. Cl.
*C08G 59/14* (2006.01)
(52) U.S. Cl. ........ 525/533; 525/403; 525/408; 525/523; 528/403; 528/418; 528/419; 528/421; 568/62; 568/63
(58) Field of Classification Search .................. 525/403, 525/408, 523, 533; 528/403, 418, 419, 421; 568/62, 63
See application file for complete search history.

(56) References Cited

U.S. PATENT DOCUMENTS

| 3,310,601 A | | 3/1967 | De Acetis et al. | |
|---|---|---|---|---|
| 3,394,098 A | | 7/1968 | McLay | |
| 4,882,216 A | * | 11/1989 | Takimoto et al. | 428/209 |
| 6,495,653 B1 | | 12/2002 | Kinsho | |
| 6,765,116 B2 | | 7/2004 | Edwards | |
| 2005/0153231 A1 | * | 7/2005 | Katoh et al. | 430/270.1 |
| 2010/0047713 A1 | * | 2/2010 | Murofushi | 430/281.1 |

FOREIGN PATENT DOCUMENTS

| JP | 59-182817 A | | 10/1984 |
|---|---|---|---|
| JP | 4-21693 B | | 4/1992 |
| JP | 08-269203 A | | 10/1996 |
| JP | 2003-252918 A | | 9/2003 |
| JP | 2004-264435 A | | 9/2004 |
| WO | 99/54373 A1 | | 10/1999 |
| WO | WO 2008/062707 | * | 5/2008 |

OTHER PUBLICATIONS

"Sosetsu Epokishi Jushi (General Reviews Epoxy Resins)", vol. 1, Basic Edition, p. 204, Nov. 19, 2003.

* cited by examiner

*Primary Examiner* — David W Wu
*Assistant Examiner* — Robert Jones, Jr.
(74) *Attorney, Agent, or Firm* — Sughrue Mion, PLLC

(57) ABSTRACT

It is an object of the present invention to provide an epoxy resin curing agent which has a favorable pot life and good storage stability as a curing agent for epoxy resins and from which an epoxy resin cured product having good water resistance and hardness is obtained through curing. The present invention is an epoxy resin curing agent containing a secondary or tertiary branched thiol compound having a substituent on a carbon atom at the α-position to a thiol group, and is also an epoxy resin composition comprising a polyvalent epoxy compound and the epoxy resin curing agent.

20 Claims, No Drawings

EPOXY RESIN CURING AGENT, PROCESS FOR PREPARING THE SAME, AND EPOXY RESIN COMPOSITION

CROSS REFERENCE TO RELATED APPLICATIONS

This application is a National Stage of International Application No. PCT/JP2008/072266 filed Dec. 8, 2008, the contents of which are incorporated herein by reference in their entirety.

TECHNICAL FIELD

The present invention relates to a curing agent for epoxy resins, which contains a thiol compound having a branch (substituent) on a carbon atom at the α-position to a thiol group (—SH), and an epoxy resin composition using the curing agent. More particularly, the invention relates to an epoxy resin curing agent having a favorable pot life and also having excellent storage stability and an epoxy resin composition using the curing agent.

BACKGROUND ART

Compounds having two or more thiol groups in one molecule readily react with epoxy resins, urethane resins or the like by mixing them with such resins and become cured products, and therefore, they have been widely used for sealing materials, coating materials, adhesives, etc. For example, various polythiol-based curing agents are described as low-temperature curing agents on page 204 of "Sosetsu Epokishi Jushi (General Reviews Epoxy Resins)" (Vol. 1, Basic Edition, published on Nov. 19, 2003). The conventional polythiol-based epoxy curing agents, however, have a defect that when such a curing agent is mixed with an epoxy compound and a curing assistant at ordinary temperature to form an epoxy resin composition, the pot life of the composition is as short as 3 minutes to 5 minutes and curing is initiated in the course of preparation of the composition, though the curing agent shows excellent curability at low temperatures.

Moreover, there is a problem that storage stability cannot be obtained because the thiol group has high reactivity to various functional groups.

As the compound having a thiol group, which is used for a curing agent for epoxy resins, a compound having a primary thiol group has been heretofore used. The compound having a primary thiol group, however, has a problem that its pot life is so short that the working conditions are restricted, though curing of the compound is accelerated by an amine catalyst.

(1) In Japanese Patent Laid-Open Publication No. 269203/1996, there is disclosed a thiol group-containing polyether polymer obtained by allowing a halogen-terminated polyether polymer which is obtained by addition of epihalohydrin to a polyol having a polyether moiety in the main chain and having 3 or more hydroxyl groups at the ends to react with an alkali hydrosulfide and/or an alkali polysulfide in amides.

It is indicated that an epoxy resin composition containing this polyether polymer has favorable curability, but when this epoxy resin composition is used as a curing agent for epoxy resins, the pot life is so short that curing is initiated while the epoxy resin and a thiol compound that is a curing agent are being mixed with each other, and hence, the working conditions are restricted. Moreover, there is no description of storage stability of the epoxy resin composition, and in the case of long term storage, there is a fear that curing is initiated during storage.

(2) An epoxy resin curing composition using a hetero ring-containing compound, which is described in International Publication No. WO99/54373, has low-temperature curability and rapid curability at ordinary temperature, but the workability is poor because its pot life is short.

(3) In Japanese Patent Publication No. 21693/1992, there is disclosed a liquid polysulfide polymer for epoxy resin curing, which is a copolymer obtained by allowing a mixture of a tri- or tetrafunctional alkyl halide and a bifunctional alkyl halide to react with an alkali polysulfide, the amount of said polyfunctional monomers in the polymerization being 20 to 60% by mol based on all the monomers, and which contains 2 to 30% by mass of end thiol groups. It is indicated that by using this liquid sulfide polymer in combination with an amine, the curing rate becomes higher as compared with that of conventional polysulfide polymers. However, the pot life is short, and the resulting cured product has a problem of workability because it develops odor, though it is excellent in impact resistance, chemical resistance, etc.

Patent document 1: Japanese Patent Laid-Open Publication No. 269203/1996
Patent document 2: International Publication No. WO99/54373
Patent document 3: Japanese Patent Publication No. 21693/1992

DISCLOSURE OF THE INVENTION

Problem to be Solved by the Invention

It is an object of the present invention to provide a curing agent for epoxy resins, which has a favorable pot life and has storage stability and from which an epoxy resin cured product having excellent water resistance and hardness is obtained by curing, and to provide a composition containing the curing agent.

Means to Solve the Problem

In view of the above object, the present inventors have earnestly studied, and as result, they have found that a thiol compound having a branch (substituent) on a carbon atom at the α-position to a thiol group (—SH) is a curing agent for epoxy resins, which has a favorable pot life and also has excellent storage stability, and that an epoxy resin cured product obtained by curing it is excellent in water resistance and hardness, so that the above problems can be solved.

The present inventors have also found that by the use of a thiol compound having at least one hydroxyl group in combination, the pot life can be controlled.

That is to say, the present invention is summarized as follows.

[1] An epoxy resin curing agent containing a thiol compound (P) having at least one substituent on a carbon atom at the α-position to a thiol group.

[2] The epoxy resin curing agent as stated in [1], wherein at least one of the substituents each being on a carbon atom at the α-position to a thiol group in the thiol compound (P) is an alkyl group.

[3] The epoxy resin curing agent as stated in [2], wherein the alkyl group is a straight-chain or branched alkyl group of 1 to 10 carbon atoms.

[4] The epoxy resin curing agent as stated in any one of [1] to [3], wherein the thiol compound (P) is a compound containing at least two thiol groups.

[5] The epoxy resin curing agent as stated in any one of [1] to [4], wherein the thiol compound (P) is represented by the following formula (1):

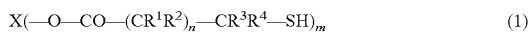

wherein X is an m-valent aliphatic or aromatic residue of at most 20 carbon atoms, which may have a substituent,
$R^1$ and $R^2$ are each independently a hydrogen atom or an alkyl group of 1 to 10 carbon atoms,
$R^3$ and $R^4$ are each independently a hydrogen atom or an alkyl group of 1 to 10 carbon atoms, and at least one of them is an alkyl group of 1 to 10 carbon atoms,
n is an integer of 0 to 4, and
m is an integer of 2 to 8.

[6] The epoxy resin curing agent as stated in any one of [1] to [4], wherein the thiol compound (P) is represented by the following formula (2):

wherein X is an m-valent aliphatic or aromatic residue of at most 20 carbon atoms, which may have a substituent,
$R^1$ and $R^2$ are each independently a hydrogen atom or an alkyl group of 1 to 10 carbon atoms,
$R^3$ and $R^4$ are each independently a hydrogen atom or an alkyl group of 1 to 10 carbon atoms, and at least one of them is an alkyl group of 1 to 10 carbon atoms, and
m is an integer of 2 to 8.

[7] The epoxy resin curing agent as stated in any one of [1] to [4], wherein the thiol compound (P) is represented by the following formula (3):

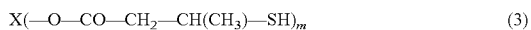

wherein X is an m-valent aliphatic or aromatic residue of at most 20 carbon atoms, which may have a substituent, and
m is an integer of 2 to 8.

[8] The epoxy resin curing agent as stated in any one of [1] to [7], wherein the thiol equivalent of the thiol compound (P), as defined as a molecular weight based on one thiol group, is in the range of 100 to 500.

[9] The epoxy resin curing agent as stated in any one of [5] to [7], wherein X has substituents and at least one of them is a hydroxyl group.

[10] The epoxy resin curing agent as stated in [9], wherein the hydroxyl group equivalent of the thiol compound (P), as defined as a molecular weight based on one hydroxyl group, is in the range of 100 to 1000.

[11] The epoxy resin curing agent as stated in any one of [5] to [10], wherein the thiol compound (P) is at least one compound selected from the group consisting of ethylene glycol bis (3-mercaptobutyrate), 1,2-propylene glycol bis (3-mercaptobutyrate), 1,3-propylene glycol bis(3-mercaptobutyrate), 1,4-butanediol bis(3-mercaptobutyrate), 2,2-bis(3-(3-mercaptobutyryloxy)-2-hydroxypropyloxyphenyl)propane, glycerol tris(3-mercaptobutyrate), trimethylolpropane tris(3-mercaptobutyrate), trimethylolpropane bis(3-mercaptobutyrate), trimethylolethane bis(3-mercaptobutyrate), pentaerythritol bis(3-mercaptobutyrate), trimethylolethane tris(3-mercaptobutyrate), pentaerythritol tris(3-mercaptobutyrate), tris(3-mercaptobutyryloxyethyl) isocyanurate, a compound wherein two 3-mercaptobutanoic acids have undergone addition to tris(2-hydroxyethyl)isocyanurate, pentaerythritol tetrakis(3-mercaptobutyrate), dipentaerythritol pentakis(3-mercaptobutyrate), bisphenol A dihydroxyethyl ether-3-mercaptobutyrate, 4,4'-(9-fluorenylidene)bis(2-phenoxyethyl(3-mercaptobutyrate)), ethylene glycol bis(3-mercaptovalerate), trimethylolpropane tris(3-mercaptovalerate), trimethylolpropane bis(3-mercaptovalerate), pentaerythritolbis(3-mercaptovalerate), pentaerythritol tris(3-mercaptovalerate), pentaerythritol tetrakis (3-mercaptovalerate), ethylene glycol bis(3-mercaptoisovalerate), trimethylolpropane bis(3-mercaptoisovalerate), pentaerythritol bis(3-mercaptoisovalerate), trimethylolpropane tris(3-mercaptoisovalerate), pentaerythritol tris(3-mercaptoisovalerate) and pentaerythritol tetrakis(3-mercaptoisovalerate).

[12] An epoxy resin composition comprising a polyvalent epoxy compound and the epoxy resin curing agent as stated in any one of [1] to [11].

[13] The epoxy resin composition as stated in [12], wherein the polyvalent epoxy compound is a glycidyl ether compound of a polyhydric alcohol.

[14] An adhesive comprising a polyvalent epoxy compound, a curing assistant and the epoxy resin curing agent as stated in any one of [1] to [11].

[15] A process for preparing an epoxy resin curing agent, comprising allowing a polyhydric alcohol to react with a thiol compound (Q) represented by the following formula (4):

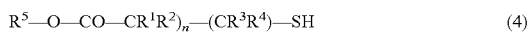

wherein $R^1$ and $R^2$ are each independently a hydrogen atom or an alkyl group of 1 to 10 carbon atoms, $R^3$ and $R^4$ are each independently a hydrogen atom or an alkyl group of 1 to 10 carbon atoms and at least one of them is an alkyl group of 1 to 10 carbon atoms, $R^5$ is a hydrogen atom, an aliphatic group of 1 to 12 carbon atoms which has a straight-chain, branched or cyclic structure or an organic group having an aromatic ring, and n is an integer of 0 to 4.

Effect of the Invention

According to the present invention, an epoxy resin curing agent having a favorable pot life and having good storage stability can be provided by the use of a thiol compound having a branch (substituent) on carbon at the α-position to a thiol group (—SH). Moreover, by the use of a thiol compound which is represented by the aforesaid formula (1) and has X having at least one hydroxyl group as a substituent, in addition to the above thiol compound, control of a pot life can be carried out. By carrying out reaction under reduced pressure in the preparation of the epoxy resin curing agent, odor can be reduced. According to the present invention, furthermore, an epoxy resin composition capable of forming an epoxy resin cured product having good water resistance and hardness can be provided.

BEST MODE FOR CARRYING OUT THE INVENTION

Embodiments of the present invention are described in detail hereinafter.
[1] Epoxy Resin Curing Agent
The epoxy resin curing agent of the application concerned contains a thiol compound having at least one substituent on a carbon atom at the α-position to a thiol group (also referred to as a "thiol compound (P)" hereinafter). The expression "having at least one substituent on a carbon atom at the α-position to a thiol group" means that the carbon atom at the α-position to a thiol group is a secondary carbon atom or a tertiary carbon atom. The expression "α-position to a thiol group" means a position of a carbon atom to which a thiol group is directly bonded.

It is preferable that at least one of the substituents is an alkyl group. It is more preferable that this alkyl group is a straight-chain or branched alkyl group of 1 to 10 carbon atoms.

The thiol compound (P) preferably contains at least two thiol groups.

The thiol compound (P) of the invention has a structure represented by, for example, the following formula (1), and has a substituent on a carbon atom at the α-position to a thiol group.

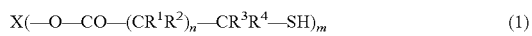

In the formula (1), X is an m-valent aliphatic or aromatic residue of at most 20 carbon atoms, which may have a substituent, $R^1$ and $R^2$ are each independently a hydrogen atom or an alkyl group of 1 to 10 carbon atoms, $R^3$ and $R^4$ are each independently a hydrogen atom or an alkyl group of 1 to 10 carbon atoms and at least one of them is an alkyl group of 1 to 10 carbon atoms, n is an integer of 0 to 4, and m is an integer of 2 to 8.

In the formula (1), $R^1$ and $R^2$ are each a hydrogen atom or an alkyl group of 1 to 10 carbon atoms. From the viewpoint of a balance between water resistance and Shore D hardness, $R^1$ and $R^2$ are each preferably a hydrogen atom or an alkyl group of 1 to 6 carbon atoms, more preferably a hydrogen atom or an alkyl group of 1 to 4 carbon atoms, still more preferably a hydrogen atom or an alkyl group of 1 or 2 carbon atoms.

In the formula (1), $R^3$ and $R^4$ are each a hydrogen atom or an alkyl group of 1 to 10 carbon atoms, and at least one of them is an alkyl group of 1 to 10 carbon atoms. That is to say, the thiol compound (P) represented by the above formula (1) is secondary or tertiary thiol. From the viewpoint of a balance between pot life and storage stability, any one of $R^3$ and $R^4$ is preferably a hydrogen atom or an alkyl group of 1 to 6 carbon atoms, more preferably a hydrogen atom or an alkyl group of 1 to 4 carbon atoms, still more preferably a hydrogen atom or an alkyl group of 1 or 2 carbon atoms.

For example, a compound wherein $R^1$ and $R^2$ are both hydrogen atoms, one of $R^3$ and $R^4$ is a hydrogen atom, and the other is a methyl group, namely, a compound represented by the following formula (3) is preferable for the reason that the balance between pot life and storage stability and properties such as water resistance and Shore D hardness are good and for the reason concerning preparation process that this compound can be prepared by the addition reaction of a SH group to α,β-unsaturated ketone.

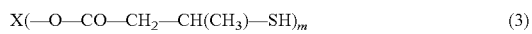

In the formula (3), X is an m-valent aliphatic or aromatic residue of at most 20 carbon atoms, which may have a substituent, and m is an integer of 2 to 8.

In the formula (1), X is an m-valent aliphatic or aromatic residue of at most 20 carbon atoms, which may have a substituent. From the viewpoints of water resistance and hardness, X preferably has 1 to 15 carbon atoms, more preferably has 1 to 12 carbon atoms, and still more preferably has 1 to 9 carbon atoms. When X has no substituent, a divalent to tetravalent aliphatic hydrocarbon group of 1 to 6 carbon atoms is particularly preferable.

When X has substituent, the substituent is, for example, a hydroxyl group, an alkyl group, an alkylene group, an aryl group, a carboxyl group, a carbonyl group, an amino group, a nitro group or a functional group containing an ether linkage, an ester linkage or a urethane bond. Of these, a hydroxyl group is particularly preferable. When X has substituent, the number of the substituents is preferably 1 to 3 though it is not specifically restricted. When X has substituent, a divalent to tetravalent aliphatic residue having 1 to 6 carbon atoms and having 1 to 3 hydroxyl groups as substituents is particularly preferable.

The valence of X in the case where X has substituent is a number obtained by subtracting the number of substituents in this case from the valence of X in the case where X has no substituent. For example, if the thiol compound (P) is derived from a compound having 4 hydroxyl groups and if one hydroxyl group remains as a substituent in the thiol compound (P), the valence of X is 3.

X sometimes represents an ether linkage, an ester linkage, a urethane bond or the like.

The epoxy resin curing agent containing the thiol compound (P) has a longer pot life as compared with conventional epoxy resin curing agents The thiol compounds (P) may be used in combination of two or more kinds. For example, when a thiol compound (P) wherein X does not have a hydroxyl group as a substituent is used in combination with a thiol compound (P) wherein at least one of the substituents of X is a hydroxyl group, the pot life is extended by the effect of the former thiol compound (P), while the thus extended time is shortened by the effect of the latter thiol compound (P). That is to say, by the use of the latter thiol compound (P) in combination, extension width of the pot life can be controlled, and adjustment of the pot life becomes possible. In this case, the former can be called a curing agent, and the latter can be called a curing assistant.

m is an integer of 2 to 8. From the viewpoint of a balance between pot life and storage stability, m is preferably 2 to 6, more preferably 2 to 4.

n is an integer of 0 to 4. n is preferably 1 because improvement in water resistance and improvement in Shore D hardness become possible. Also from the viewpoint of ease of obtaining raw materials, 1 is preferable. That is to say, a compound represented by the following formula (2) is preferable, and a compound represented by the following formula (3) is more preferable.

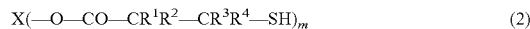

In the formula (2), X is an m-valent aliphatic or aromatic residue of at most 20 carbon atoms, which may have a substituent, $R^1$ and $R^2$ are each independently a hydrogen atom or an alkyl group of 1 to 10 carbon atoms, $R^3$ and $R^4$ are each independently a hydrogen atom or an alkyl group of 1 to 10 carbon atoms and at least one of them is an alkyl group of 1 to 10 carbon atoms, and m is an integer of 2 to 8.

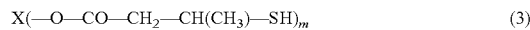

In the formula (3), X is an m-valent aliphatic or aromatic residue of at most 20 carbon atoms, which may have a substituent, and m is an integer of 2 to 8.

Examples of the thiol compounds (P) include:
ethylene glycol bis(3-mercaptobutyrate), 1,2-propylene glycol bis(3-mercaptobutyrate), 1,3-propylene glycol bis(3-mercaptobutyrate), 1,4-butanediol bis(3-mercaptobutyrate), 2,2-bis(3-(3-mercaptobutyryloxy)-2-hydroxypropyloxyphenyl)propane, glycerol tris(3-mercaptobutyrate), trimethylolpropane tris(3-mercaptobutyrate), trimethylolpropane bis(3-mercaptobutyrate), trimethylolethane bis(3-mercaptobutyrate), pentaerythritol bis(3-mercaptobutyrate), trimethylolethane tris(3-mercaptobutyrate), pentaerythritol tris(3-mercaptobutyrate), tris(3-mercaptobutyryloxyethyl)isocyanurate, a compound wherein two 3-mercaptobutanoic acids have undergone addition to tris(2-hydroxyethyl)isocyanurate, pentaerythritol tetrakis(3-mercaptobutyrate), dipentaerythritol pentakis(3-mercaptobutyrate), bisphenol A dihydroxyethyl ether-3-mercaptobutyrate, 4,4'-(9-fluorenylidene)bis(2-phenoxyethyl(3-mercaptobutyrate));

ethylene glycol bis(3-mercaptovalerate), trimethylolpropane tris(3-mercaptovalerate), trimethylolpropane bis(3-mercaptovalerate), pentaerythritol bis(3-mercaptovalerate), pentaerythritol tris(3-mercaptovalerate), pentaerythritol tetrakis(3-mercaptovalerate);

ethylene glycol bis(3-mercaptoisovalerate), trimethylolpropane bis(3-mercaptoisovalerate), pentaerythritol bis(3-mercaptoisovalerate), trimethylolpropane tris(3-mercaptoisovalerate), pentaerythritol tris(3-mercaptoisovalerate) and pentaerythritol tetrakis(3-mercaptoisovalerate).

The compound wherein two 3-mercaptobutanoic acids have undergone addition to tris(2-hydroxyethyl)isocyanurate is, for example, 3-mercaptobutanoic acid 2-[3-(2-hydroxy)-5-(2-(3-mercaptobutyryloxy)ethyl)-2,4,6-trioxo-[1,3,5]triazinan-1-yl]ethyl ester.

By the use of the thiol compound (P) as a curing agent for epoxy resins, a cured product having a favorable pot life, having excellent storage stability and also having good water resistance and hardness can be obtained. By the use of a thiol compound (P) having at least one hydroxyl group in combination, extension width of the pot life can be controlled, and adjustment of the pot life becomes possible. That is to say, high qualities can be achieved on various articles made from the cured product of the invention.

Examples of the thiol compounds (P) having at least one hydroxyl group include:

glycerol bis(3-mercaptobutyrate), trimethylolpropane bis (3-mercaptobutyrate), trimethylolethane bis(3-mercaptobutyrate), pentaerythritolbis(3-mercaptobutyrate), pentaerythritol tris(3-mercaptobutyrate), dipentaerythritol pentakis(3-mercaptobutyrate), a compound wherein two 3-mercaptobutanoic acids have undergone addition to tris(2-hydroxyethyl)isocyanurate;

trimethylolpropanebis(3-mercaptovalerate), pentaerythritol bis(3-mercaptovalerate), pentaerythritol tris(3-mercaptovalerate);

trimethylolpropane bis(3-mercaptoisovalerate), pentaerythritol bis(3-mercaptoisovalerate) and pentaerythritol tris(3-mercaptoisovalerate).

The compound wherein two 3-mercaptobutanoic acids have undergone addition to tris(2-hydroxyethyl)isocyanurate is, for example, 3-mercaptobutanoic acid 2-[3-(2-hydroxyl)-5-(2-(3-mercaptobutyryloxy)ethyl)-2,4,6-trioxo-[1,3,5]triazinan-1-yl]ethyl ester. Preferable are pentaerythritol tris(3-mercaptobutyrate) and trimethylolpropane bis(3-mercaptobutyrate). These can be used singly or can be used in combination of two or more kinds in arbitrary proportions.

Although the thiol equivalent of the thiol compound (P) is not specifically restricted, it is in the range of preferably 100 to 500, more preferably 100 to 400, still more preferably 100 to 300.

The thiol equivalent is a molecular weight based on one thiol group. The thiol equivalent is measured by an iodine titration method and is specifically measured by dissolving 0.2 g of the thiol compound (P) in 20 ml of chloroform, adding 10 ml of isopropanol, 20 ml of water and 1 ml of a starch indicator and then performing titration with an iodine solution.

Although the hydroxyl group equivalent of the thiol compound (P) is not specifically restricted either, it is in the range of preferably 100 to 1000, more preferably 100 to 800, still more preferably 100 to 600.

The hydroxyl group equivalent is a molecular weight based on one hydroxyl group. The hydroxyl group equivalent is measured by an acetyl chloride-potassium hydroxide titration method and is specifically measured by acetylating a hydroxyl group of the thiol compound (P) in pyridine using acetyl chloride, then decomposing an excess reagent with water and titrating the resulting acetic acid with a potassium hydroxide-methanol solution.

The epoxy resin curing agent according to the invention may be composed of only the thiol compound, or may contain other curing agent components. Examples of the other curing agent components include polyamine, polyamidoamine, acid anhydride, dicyandiamide, phenol and imidazole.

[II] Process for Preparing Epoxy Resin Curing Agent

The thiol compound (P) used for the epoxy resin curing agent of the invention is obtained by, for example, allowing (i) a polyhydric alcohol to react with (ii) a thiol compound (Q) having a substituent on a carbon atom at the α-position to a thiol group and containing an oxycarbonyl group or a carbonyloxy group (also referred to as a "thiol compound (Q)" simply hereinafter) (iii) in the presence of an acid catalyst or in the absence of a catalyst.

(i) The polyhydric alcohol for use in the invention is represented by the following formula (5).

$$X(OH)_t \qquad (5)$$

In the formula (5), X has the same meaning as that of X in the aforesaid formula (1), and t is an integer of 2 to 8.

Examples of such polyhydric alcohols include:

dihydric alcohols, such as ethylene glycol, diethylene glycol, triethylene glycol, tetraethylene glycol, polyethylene glycol, propylene glycol, dipropylene glycol, tripropylene glycol, polypropylene glycol, neopentyl glycol, 1,2-propanediol, 1,3-propanediol, 1,3-butanediol, 1,4-butanediol, 1,2-pentanediol, 1,3-pentanediol, 2,3-pentanediol, 1,4-pentanediol, 1,5-pentanediol, 1,6-hexanediol, 1,9-nonanediol, tricyclodecane dimethanol, 2,2-bis(2-hdyroxyethoxyphenyl) propane, bisphenol A alkylene oxide adduct, bisphenol F alkylene oxide adduct, bisphenol S alkylene oxide adduct, 1,4-cyclohexanediol, 1,4-cyclohexanedimethanol, 1,2-hexanediol, 1,3-hexanediol, 2,3-hexanediol, 1,4-hexanediol, 2,4-hexanediol, 3,4-hexanediol, 1,5-hexanediol, 2,5-hexanediol, 1,6-hexanediol and 9,9-bis[4-(2-hydroxyethyl)phenyl]fluorene; and tri- or higher hydric alcohols, such as glycerol, diglycerol, trimethylolethane, trimethylolpropane, ditrimethylolpropane, tris(2-hdyroxyethyl)isocyanurate, hexanetriol, sorbitol, pentaerythritol, dipentaerythritol and sucrose.

Of the above alcohols, tri- or higher hydric alcohols are preferable from the viewpoints of pot life and hardness.

When the polyhydric alcohol is a tri- or higher hydric alcohol, at least two hydroxyl groups have only to react with the thiol compound (Q), and a hydroxyl group may remain.

Instead of the polyhydric alcohol, a polyamine can be used, and examples thereof include triethanolamine, ethylenediamine, diethylenetriamine, triethylenetetramine, tetraethylenepentamine, 1,6-hexamethylenediamine, 1,8-octamethylenediamine, 1,12-dodecamethylenediamine, o-phenylenediamine, m-phenylenediamine, p-phenylenediamine, o-xylylenediamine, m-xylylenediamine, p-xylylenediamine, menthanediamine, bis(4-amino-3-methylcyclohexyl)methane, isophoronediamine, 1,3-diaminocyclohexane and spiroacetal-based amine.

(ii) The thiol compound (Q) for use in the invention is a thiol compound having a substituent on a carbon atom at the α-position to a thiol group and containing an oxycarbonyl group or a carbonyloxy group. Of such compounds, a compound wherein at least one of the substituents each being on a carbon atom at the α-position to a thiol group is an alkyl group is preferable, and the alkyl group is preferably a straight-chain or branched alkyl group of 1 to 10 carbon atoms.

Such a compound is represented by, for example, the following formula (4).

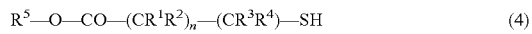

$$R^5\text{—}O\text{—}CO\text{—}(CR^1R^2)_n\text{—}(CR^3R^4)\text{—}SH \quad (4)$$

In the above formula, $R^1$ and $R^2$ are each independently a hydrogen atom or an alkyl group of 1 to 10 carbon atoms, $R^3$ and $R^4$ are each independently a hydrogen atom or an alkyl group of 1 to 10 carbon atoms and at least one of them is an alkyl group of 1 to 10 carbon atoms, $R^5$ is a hydrogen atom, an aliphatic group of 1 to 12 carbon atoms which has a straight-chain, branched or cyclic structure or an organic group having an aromatic ring, and n is an integer of 0 to 4.

$R^1$, $R^2$, $R^3$, $R^4$ and n in the formula (4) have the same meanings as those of $R^1$, $R^2$, $R^3$, $R^4$ and n in the aforesaid formula (1).

$R^5$ is a hydrogen atom, an aliphatic group of 1 to 12 carbon atoms which has a straight-chain, branched or cyclic structure, or an organic group having an aromatic ring. From the viewpoint of reactivity, $R^5$ is preferably a hydrogen atom or an aliphatic group of 1 to 6 carbon atoms which has a straight-chain or branched structure, $R^5$ is more preferably a hydrogen atom or an aliphatic group of 1 to 4 carbon atoms which has a straight-chain or branched structure, and $R^5$ is still more preferably a hydrogen atom or an aliphatic group of 1 or 2 carbon atoms which has a straight-chain structure.

Examples of the thiol compounds (Q) include 2-mercaptopropionic acid, 3-mercaptobutyric acid, 2-mercaptoisobutyric acid, 3-mercaptoisobutyric acid, 3-mercapto-3-methylbutyric acid, 2-mercaptovaleric acid, 4-mercaptovaleric acid, 3-mercaptoisovaleric acid, methyl 3-mercaptobutanoate, ethyl 3-mercaptobutanoate, methyl 4-mercaptovalerate, ethyl 4-mercaptovalerate, methyl 3-mercaptoisovalearate, methyl 3-mercaptoisovalerate and 2-mercaptopropionic acid ethyl ester.

The thiol compound (Q) can contain two or more thiol groups.

With regard to the molar ratio between the polyhydric alcohol and the thiol compound (Q) in the reaction of them, the thiol compound (Q) can be used in an amount of usually 1 to 1.5 mol based on 1 mol of the hydroxyl group in the polyhydric alcohol, but in the case where a hydroxyl group may remain, the molar ratio is not specifically restricted.

(iii) In the preparation of the thiol compound (P) of the invention, an acid catalyst can be also used. By the use of the acid catalyst, the reaction rate can be increased.

Although the acid catalyst is not specifically restricted, it is preferably a protonic acid, and for example, p-toluenesulfonic acid, naphthalenesulfonic acid, camphorsulfonic acid, benzenesulfonic acid, o-toluenesulfonic acid, methanesulfonic acid, ethanesulfonic acid, butanesulfonic acid, isobutanesulfonic acid, trifluoromethanesulfonic acid, sulfuric acid, hydrochloric acid, phosphoric acid, acetic acid, trifluoroacetic acid, H type ion-exchange resin or the like is employable.

The above acid catalysts may be used singly or may be used in combination of two or more kinds. The amount of the acid catalyst added is in the range of preferably 0.1 to 15% by mol, more preferably 0.5 to 10% by mol, based on 1 mol of the polyhydric alcohol. If the amount thereof exceeds 15% by mol, there is a possibility of occurrence of side reaction during the reaction. If the amount thereof is less than 0.1% by mol, the catalytic effect of increasing the reaction rate is not obtained.

When the reaction of the polyhydric alcohol with the thiol compound (Q) is carried out under reduced pressure, a solvent is usually unnecessary, but the solvent can be used when needed, for example, in the case of azeotropy with water or an alcohol formed as a side product.

When the reaction is carried out at normal pressure, various solvents are employable, and examples of the solvents include toluene, xylene, ethylbenzene, chlorobenzene, dichlorobenzene and trichlorobenzene. These solvents may be used singly or may be used in combination of two or more kinds in arbitrary proportions.

Although the amount of the reaction solvent used is not specifically restricted, the solvent can be used in an amount of 5 to 200 parts by mass based on 10 parts by mass of the polyhydric alcohol, and the solvent is preferably used in an amount of 10 to 100 parts by mass.

In the present invention, the reaction can be carried out at a pressure lower than the atmospheric pressure, that is, under the reduced pressure conditions. By carrying out the reaction under the reduced pressure conditions, an odor component can be removed, and as a result, odor of the curing agent containing the thiol compound (P) can be reduced.

Moreover, by virtue of reduced pressure, the reaction can be carried out with distilling off water or an alcohol formed as a side product, and by accelerating the reaction, shortening of the reaction time and improvement in productivity can be achieved.

The reaction pressure is preferably a low pressure, and specifically, the reaction is carried out at a pressure of preferably 1 to 400 mmHg, more preferably 1 to 300 mmHg.

The pressure conditions in the preparation of the thiol compound (P) are not limited to the reduced pressure conditions, and the preparation can be also carried out at normal pressure.

The reaction temperature in the reaction of the polyhydric alcohol with the thiol compound (Q) is in the range of 80 to 160° C., preferably 100 to 140° C.

By carrying out the reaction under the above conditions, side reaction can be inhibited, and the thiol compound (P) can be obtained with excellent yield and purity.

[III] Epoxy Resin Composition

The epoxy resin composition of the invention contains (A) an epoxy resin that is a polyvalent epoxy compound which becomes a main agent and (B) the above-mentioned epoxy resin curing agent, and can further contain (C) a curing assistant.

The epoxy resin curing agent (B) contains the thiol compound (P). This thiol compound (P) can be used as a curing agent for the epoxy resin (A).

Examples of the epoxy resins (A) include polyhydric phenols, such as bisphenol A, halogenated bisphenol A, bisphenol F, halogenated bisphenol F, resorcinol, hydroquinone, pyrocatechol, 4,4'-dihydroxybiphenyl and 1,5-hydroxynaphthalene, polyhydric alcohols, such as ethylene glycol, propylene glycol and glycerol, and epoxy resins obtained by the addition of epichlorohydrin to aromatic dicarboxylic acids such as oxybenzoic acid and phthalic acid, but the epoxy resins are not limited to these resins. As the epoxy resin (A), a glycidyl ether compound of a polyhydric alcohol is particularly preferable.

Examples of commercially available epoxy resin products include Epicoat 828, 1001, 801, 806, 807, 152, 604, 630, 871, YX8000, YX8034, YX4000 and Cardura E10P (from Japan Epoxy Resins Co., Ltd.), Epichlon 830, 835LV, HP4032D, 703, 720 and HP820 (from Dainippon Ink & Chemicals, Inc.), EP4100, EP4000, EP4080, EP4085, EP4088, EPU6, EPR4023, EPR1309 and EP49-20 (from ADEKA Corporation), Denachol EX411, EX314, EX201, EX212, EX252, EX111, EX146 and EX721 (from Nagase ChemteX Corporation), and KBM403 and KBE402 (from Shin-Etsu Chemical Co., Ltd.), but the epoxy resin products are not limited to these products. These resins can be used singly or can be used in combination of two or more kinds in arbitrary proportions.

To the epoxy resin composition of the invention, a curing assistant (C) can be added in order to accelerate curing reaction of the epoxy resin (A) with the thiol compound (P) contained in the epoxy resin curing agent (B).

As the curing assistant (C), a basic compound is employable. Examples of the basic compounds include trimethylamine, triethylamine, tetraethylmethylenediamine, tetramethylpropane-1,3-diamine, tetramethylhexane-1,6-diamine, pentamethyldiethylenetriamine, pentamethyldipropylenetriamine, bis(2-dimethylaminoethyl)ether, ethylene glycol (3-dimethyl)aminopropyl ether, dimethylaminoethanol, dimethylaminoethoxyethanol, N,N,N'-trimethylaminoethylethanolamine, dimethylcyclohexylamine, N,N-dimethylaminomethylphenol, N,N-dimethylpropylamine, N,N,N',N'-tetramethylhexamethylenediamine, N-methylpiperidine, N,N'-dimethylpiperazine, N,N-dimethylbenzylamine, dimethylaminomethylphenol, 2,4,6-tris(dimethylaminomethyl)phenol, 1,8-diazabicyclo[5.4.0]undecene-7, 1,5-diazabicyclo[4.3.0]-nonene-5,6-dibutylamino-1,8-diazabicyclo[5.4.0]undecene-7, 1,2-dimethylimidazole, dimethylpiperazine, N-methyl-N'-(2-dimethylamino)-ethylpiperazine, N-methylmorpholine, N-(N',N'-(dimethylamino)ethyl)morpholine, N-methyl-N'-(2-hydroxyethyl)morpholine, triethylenediamine and hexamethylenetetramine. Of these, tertiary amines are preferable, and N,N-dimethylbenzylamine and 2,4,6-tris(dimethylaminomethyl)phenol are particularly preferable. These can be used singly or can be used in combination of two or more kinds in arbitrary proportions.

As the curing assistant (C), a phosphorus atom-containing compound is also employable. Examples of the phosphorus atom-containing compounds include ethylphosphine, phenylphosphine, dimethylphosphine, diphenylphosphine, trimethylphosphine, triethylphosphine, tributylphosphine, triphenylphosphine, tris (p-tolyl)phosphine, tris(alkylphenyl)phosphine, tris(alkoxyphenyl)phosphine, trimethyl phosphate, triethyl phosphate, triphenyl phosphate, trialkyl phosphate, tetraphenylphosphonium.tetraphenyl borate and 1,4-bis (diphenylphosphino)butane, but the curing assistants are not limited to these compounds. These can be used singly or can be used in combination of two or more kinds in arbitrary proportions.

Examples of commercially available curing assistant products include Epicure 3010 (from Japan Epoxy Resins Co., Ltd.), imidazole compound 2PZ, 2PHZ, 2P4MHZ, C17Z, 2MZ-A, 2E4MZ-CNS and 2MA-OK (from Shikoku Chemicals Corporation), Amicure PN23, PN31, PN40J, PN—H, MY24 and MY—H (from Ajinomoto Fine-Techno Co., Ltd.), EH-3293S, EH-3366S, EH-3615S, EH-4070S, EH-4342S and EH-3713S (from ADEKA Corporation), Novacure HX-3742 and HX-3721 (from Asahi Kasei Chemicals Corporation), and FXE-1000, FXR-1030, FXR-1080 and FXR-1110 (from Fuji Kasei Kogyo Co., Ltd.), but the curing assistant products are not limited to these products.

The amounts of the epoxy resin (A), the curing agent (B) and the curing assistant (C) used in the epoxy resin composition of the invention are not specifically restricted and can be properly determined according to the use purpose. The amount of the epoxy resin (A) used is in the range of preferably 0.6 to 1.7 mol, more preferably 0.7 to 1.5 mol, still more preferably 0.7 to 1.3 mol, in terms of epoxy group, based on 1 mol of a thiol group of the curing agent (B)

The amount of the curing assistant (C) used is in the range of preferably 0.01 to 15 parts by mass, more preferably 0.05 to 10 parts by mass, still more preferably 0.05 to 5 parts by mass, based on 100 parts by mass of the curing agent (B). If the amount of the curing assistant used exceeds 15 parts by mass, irritating odor becomes intense, and workability sometimes becomes poor.

The epoxy resin composition of the invention can contain, if necessary, (a) thermoplastic resins, (b) deodorizers, (c) adhesion improvers, such as silane coupling agent and titanium coupling agent, (d) antioxidants, such as hindered amines, hydroquinones and hindered phenols, (e) ultraviolet light absorbers, such as benzophenones, benzotriazoles, salicylic acid esters and metal complex salts, (f) stabilizers, such as metallic soaps, inorganic and organic salts of heavy metals (e.g., zinc, tin, lead, cadmium) and organotin compounds, (g) plasticizers, such as phthalic acid ester, phosphoric acid ester, fatty acid ester, epoxidized soybean oil, castor oil, liquid paraffin and alkyl polycyclic aromatic hydrocarbon, (h) waxes, such as paraffin wax, microcrystalline wax, polymerized wax, beeswax, spermaceti wax and low-molecular weight polyolefin, (i) non-reactive diluents, such as benzyl alcohol, tar and bitumen, (j) reactive diluents, such as low-molecular aliphatic glycidyl ether, aromatic monoglycidyl ether and (meth)acrylate esters, (k) fillers, such as calcium carbonate, kaolin, talc, mica, bentonite, clay, sericite, glass fiber, carbon fiber, aramid fiber, nylon fiber, acrylic fiber, glass powder, glass balloon, Shrasu balloon, coal powder, acrylic resin powder, phenolic resin powder, metallic powder, ceramic powder, zeolite and slate powder, (l) pigments or dyes, such as carbon black, titanium oxide, red iron oxide, para red and Prussian blue, (m) solvents, such as ethyl acetate, toluene, alcohols, ethers and ketones, (n) blowing agents, (o) dehydrating agents, such as silane coupling agent, monoisocyanate compound and carbodiimide compound, (p) antistatic agents, (q) antibacterial agents, (r) mildew proofing agents, (s) viscosity modifiers, (t) perfumes, (u) flame retardants, (v) leveling agents, (w) dispersing agents, (x) radical polymerization initiators, etc. These can be used singly or can be used in combination of two or more kinds in arbitrary proportions.

The process for preparing the epoxy resin composition of the invention is not specifically restricted as long as the materials used can be mixed and dispersed, and for example, the following processes can be thought.

(i) The components are kneaded by a stirring rod, a spatula or the like in an appropriate container, such as a glass beaker, a can, a plastic cup or an aluminum cup.

(ii) The components are kneaded by a double helical ribbon impeller, a gate impeller or the like.

(iii) The components are kneaded by a planetary mixer.

(iv) The components are kneaded by a bead mill.

(v) The components are kneaded by a three-roll mill.

(vi) The components are kneaded by en extruder type kneading extrusion machine.

The way of using the present invention is not specifically restricted, and the present invention can be used under any of the ordinary temperature conditions of 5 to 40° C. and the high temperature conditions of 40 to 200° C. A higher temperature shortens the pot life and can increase the curing rate, and therefore, a cured product can be obtained in a shorter period of time. However, there is a fear of coloring, so that the temperature is in the range of preferably 5 to 100° C., more preferably 5 to 40° C.

The epoxy resin composition of the invention and its cured product can be used for (a) coating materials and coating agents, such as heavy-duty anti-corrosion coating material, anti-corrosion coating agent, coating agent for plastered floor, coating material for exterior trim, automotive coating material, powder coating material and primer, (b) adhesives, such as adhesive for structure, elastic adhesive, solvent type reactive adhesive, bonding adhesive and pressure-sensitive adhesive, (c) sealing agents, (d) injection repairing agents for concrete, (e) matrix resins for laminates such as fiber-reinforced laminate, (f) materials for electronics, such as casting insulating material, semiconductor sealant, layer insulating material, etching resist material, plating resist and solder resist, (g) repairing putty, and (h) impregnation, pouring, molding, etc.

For example, an adhesive can be obtained by mixing the aforesaid polyvalent epoxy compound, curing assistant and epoxy resin curing agent.

EXAMPLES

The present invention is further described with reference to the following examples and comparative examples, but it should be construed that the invention is in no way restricted by the description of those examples.

The term "part(s)" in the examples means "part(s) by mass".

Synthesis Example 1

Synthesis of mixture of pentaerythritol tetrakis(3-mercaptobutyrate)(PE4MB) and pentaerythritol tris(3-mercaptobutyrate)(PE3MB)

In a 200 ml egg plant type flask, 12.5 g (91.8 mmol) of pentaerythritol (available from Tokyo Chemical Industry Co., Ltd.), 51.0 g (424 mmol) of 3-mercaptobutanoic acid (available from Yodo Chemical Co., Ltd.) and 0.93 g (4.89 mmol) of p-toluenesulfonic acid monohydrate (available from Junsei Chemical Co., Ltd.) were placed, and on the flask, a cooling pipe, an aqueous distillate trapping device and a vacuum pump were installed.

With stirring the contents in the flask, the pressure in the flask was reduced down to 10 mmHg, and the flask was heated to 90° C. After 4 hours from the beginning of refluxing, the temperature was raised to 100° C., and after another 15 minutes, the temperature was raised to 110° C. In this state, the reaction was carried out for 2.5 hours, and then the reaction solution was cooled down to room temperature. After 100 ml of toluene was added, the mixture was washed with 100 ml of pure water twice. Next, the toluene solution was subjected to neutralization washing with 100 ml of a saturated sodium hydrogencarbonate aqueous solution twice and further subjected to washing with 100 ml of pure water twice. Then, toluene was distilled off, and vacuum drying was carried out to obtain a light yellow liquid curing agent 1. Composition of the curing agent 1 is as follows. PE4MB: 91.5%; PE3MB: 3.9%; and others: pentaerythritol bis(3-mercaptobutyrate), p-toluenesulfonic acid adduct of PE3MB, disulfide of 3-mercaptobutanoic acid and 3-mercaptobutanoic acid adduct of PE4MB. The 3-mercaptobutanoic acid adduct of PE4MB is 3-(3-mercaptobutyrylsulfanyl)butanoic acid 3-(3-mercaptobutyryloxy)-2,2-bis-(3-mercaptobutyryloxymethyl)propyl ester, and the disulfide of 3-mercaptobutanoic acid is 3-(2-carboxy-1-methyl-ethyldisulfanyl)-butanoic acid. The yield of PE4MB and PE3MB in this synthetic liquid 1 was 48.9 g and was 97.8%. The thiol equivalent of PE4MB contained in the resulting curing agent 1 was 136 g/eq., and the thiol equivalent of PE3MB was 146 g/eq. The hydroxyl group equivalent of PE3MB was 443 g/eq.

Synthesis Example 2

Synthesis of trimethylolpropane tris(3-mercaptobutyrate (TPMB))

In a 200 ml egg plant type flask, 13.4 g (100 mmol) of trimethylolpropane (available from Tokyo Chemical Industry Co., Ltd.), 37.8 g (315 mmol) of 3-mercaptobutanoic acid (available from Yodo Chemical Co., Ltd.), 1.80 g (9.45 mmol) of p-toluenesulfonic acid monohydrate (available from Tokyo Chemical Industry Co., Ltd.) and 100 g of toluene were placed, and on the flask, a Dean-Stark device and a cooling pipe were installed. With stirring the contents in the flask, the flask was heated to 110° C. After 32 hours from the initiation of reaction, the reaction solution was allowed to cool and washed with pure water twice. Thereafter, the reaction solution was neutralized with 100 ml of a saturated sodium hydrogencarbonate aqueous solution. The reaction solution was further washed with pure water once, then toluene was distilled off, and vacuum drying was carried out to obtain a colorless transparent liquid curing agent 2. The yield of TPMB in this curing agent 2 was 42.4 g and was 96.3%. The thiol equivalent of TPMB contained in the resulting curing agent 2 was 144 g/eq.

Performance evaluation is illustrated below.

Materials used in the examples are as follows.

EP828: available from Japan Epoxy Resins Co., Ltd., bisphenol A type glycidyl ether, trade name: Epicoat 828 (registered trademark), epoxy equivalent: 186 g/eq.

Curing agent 1: mixture obtained in the aforesaid Synthesis Example 1 and containing PE4MB and PE3MB as main components Curing agent 2: mixture obtained in the aforesaid Synthesis Example 2 and containing TPMB as a main component PE4MB: pentaerythritol tetrakis(3-mercaptobutyrate), substance obtained by separation and purification of a mixture obtained in the aforesaid Synthesis Example 1 through silica gel column chromatography PE3MB: pentaerythritol tris(3-mercaptobutyrate), substance obtained by separation and purification of a mixture obtained in the aforesaid Synthesis Example 1 through silica gel column chromatography QX40: available from Japan Epoxy Resins Co., Ltd., tetrafunctional aliphatic polythiol (primary thiol), pentaerythritol tetrakis(3-mercaptopropionate), trade name: Epicure QX40 (registered trademark), thiol equivalent: 127 g/eq.

3-800: available from Japan Epoxy Resins Co., Ltd., polythiol, poly[oxy(methyl-1,2-ethanediyl)], a-hydro-w-(2-hydroxy-3-mercaptopropoxy)-a,a',a"-ether with 2-(hydroxymethyl)-2-methyl-1,3-propanediol, trade name: Cupcure (registered trademark) 3-800, thiol equivalent: 296 g/eq.

3010: available from Japan Epoxy Resins Co., Ltd., 2,4,6-tris(dimethylaminomethyl)phenol, trade name: Epicure 3010 (registered trademark)

TETA: available from Tokyo Chemical Industry Co., Ltd., triethylenetetramine

DMBA: available from Tokyo Chemical Industry Co., Ltd., N,N-dimethylbenzylamine

[1] Pot Life

Example 1

To 100 parts by mass of EP828 as the epoxy resin (A), 70 parts by mass of the curing agent 1 obtained in Synthesis Example 1 as the curing agent (B) and 10 parts by mass of 3010 as the curing assistant (C) were added at 25° C., and they were mixed to measure a period of time required for initiation of curing. The time when the temperature of the composition became 60° C. by virtue of heat of reaction was regarded as the time when curing was initiated. A period of time between the time when mixing was started and the time when curing was initiated was regarded as a pot life, and the pot life is set forth in Table 1.

Comparative Example 1

A pot life was measured in the same manner as in Example 1, except that 70 parts by mass of QX40 were used instead of the curing agent 1. The pot life is set forth in Table 1.

TABLE 1

|  | Ex. 1 | Comp. Ex. 1 |
|---|---|---|
| Pot life (min) | 14 | 3 |

It can be seen from Table 1 that in Example 1, the period of time required for initiation of curing was not longer than 15 minutes and the composition had a proper pot life, so that workability was favorable. On the other hand, in Comparative Example 1, the pot life is too short, and curing was initiated while the epoxy resin and the thiol compound which was a curing agent were being mixed, so that workability was poor and the working conditions were restricted.

Examples 2 to 7

A pot life of each composition having formulation shown in Table 2 was measured in the same manner as in Example 1. The pot life is set forth in Table 2. The unit of each value in compounding is part(s) by mass.

TABLE 2

|  |  | Ex. 2 | Ex. 3 | Ex. 4 | Ex. 5 | Ex. 6 | Ex. 7 |
|---|---|---|---|---|---|---|---|
| Epoxy resin | EP828 | 100 | 100 | 100 | 100 | 100 | 100 |
| Curing agent | PE4MB | 56 | 57.4 | 58.8 | 60.2 | 61.6 | 63 |
|  | PE3MB | 14 | 12.6 | 11.2 | 9.8 | 8.4 | 7 |
| Curing assistant | 3010 | 10 | 10 | 10 | 10 | 10 | 10 |
| Pot life (min) |  | 5.7 | 7.0 | 7.7 | 8.7 | 9.7 | 11.0 |

It can be seen from Table 2 that as the content of PE3MB having one hydroxyl group was increased, extension width of the pot life was decreased, and as a result, the pot life can be controlled by the use of a mixture of PE4MB and PE3MB.

[2] 60° C. Storage Stability

Examples 8 and 9, Comparative Examples 2 and 3

Each composition having formulation shown in Table 3 was placed in a constant temperature container preset at 60° C., and the number of days required for curing at 60° C. was determined. The number of days is set forth in Table 3. The unit of each value in compounding is part(s) by mass. The time when the viscosity of the composition became not lower than 1000 Pa·s at 25° C. was regarded as the time when the composition was cured. A larger number of days indicate more excellent storage stability.

TABLE 3

|  |  | Ex. 8 | Ex. 9 | Comp. Ex. 2 | Comp. Ex. 3 |
|---|---|---|---|---|---|
| Epoxy resin | EP828 | 100 | 100 |  |  |
| Curing agent | Curing agent 1 | 70 | 70 |  |  |
|  | QX40 |  |  | 70 | 70 |
| Curing assistant | TETA |  | 10 |  | 10 |
| 60° C. Storage stability (day(s)) |  | 25 or more | 25 or more | 10 | 11 |

It can be seen from Table 3 that in Examples 8 and 9 using the curing agent 1 of the invention containing PE3MB which was secondary thiol and PE4MB, the composition had excellent storage stability at 60° C. From this, it can be seen that storing of a mixture of a curing agent and an epoxy resin or a mixture of a curing agent and a curing assistant as an one-package type composition is also possible.

On the other hand, it can be seen that in Comparative Examples 2 and 3 using QX40 which was primary thiol, the composition had poor storage stability, and shortening of a pot life and storage stability were incompatible with each other.

[3] Water Resistance

Examples 10 and 11, Comparative Examples 4 and 5

[Preparation of Cured Product]

Each composition having formulation shown in Table 4 was cast into a mold having a diameter of 50 mm and a thickness of 3 mm and cured at 25° C. for 24 hours in accordance with JIS-K7209 to obtain a cured product.

The cured product obtained in the above [Preparation of cured product] was immersed in a constant temperature water bath preset at 98° C. for 24 hours and then taken out of the constant temperature water bath. From the surface of the cured product, water was thoroughly wiped off, and the weight (M2) of the cured product was measured. Using the weight (M2) and the weight (M1) before immersion, water absorption ratio ($\alpha$) was calculated from the formula (6), and the water absorption ratio is set forth in Table 4. The unit of each value in compounding is part(s) by mass. A smaller value of the water absorption ratio ($\alpha$) indicates better water resistance.

$$\alpha(\%) = (M2 - M1)/M1 \times 100 \qquad (6)$$

TABLE 4

|  |  | Ex. 10 | Ex. 11 | Comp. Ex. 4 | Comp. Ex. 5 |
|---|---|---|---|---|---|
| Epoxy resin | EP828 | 100 | 100 | 100 | 100 |
| Curing agent | Curing agent 1 | 70 |  |  |  |
|  | Curing agent 2 |  | 80 |  |  |
|  | QX40 |  |  | 70 |  |
|  | 3-800 |  |  |  | 160 |
| Curing assistant | DMBA | 3.5 | 3.5 | 3.5 | 3.5 |
| Water absorption ratio (%) |  | 3.2 | 2.6 | 5.3 | 7.1 |

It can be seen from Examples 10 and 11 that the cured product formed from the composition containing the curing agent 1 containing PE3MB which was secondary thiol and PE4MB and the cured product formed from the composition containing the curing agent 2 containing TPMB which was secondary thiol had lower water absorption ratio and more excellent water resistance as compared with such conventional thiol compounds as shown in the comparative examples.

[4] Shore D Hardness

Example 12, Comparative Example 6

From each composition having formulation shown in Table 5, a cured product was obtained in the same manner as in the above [Preparation of cured product]. Shore D hardness of the resulting cured product was measured using a hardness tester Shore type DD model (manufactured by Imai Seiki), and the Shore D hardness is set forth in Table 5. The unit of each value in compounding is part(s) by mass. Shore D hardness after the measurement of water absorption ratio in [3] was also measured in the same manner as above, and the Shore D hardness is set forth in Table 5. A larger value of Shore D hardness indicates higher hardness.

TABLE 5

|  |  | Ex. 12 | Comp. Ex. 6 |
|---|---|---|---|
| Epoxy resin | EP828 | 100 | 100 |
| Curing agent | Curing agent 1 | 70 |  |
|  | QX40 |  | 70 |
| Curing assistant | DMBA | 3.5 | 3.5 |
| Shore D hardness | Before water absorption | 72.7 | 71.8 |
|  | After water absorption | 53.8 | 11.9 |

It can be seen from Table 5 that the Shore D hardness of the cured product of Example 12 formed from the composition using the curing agent 1 containing PE3MB and PE4MB before the measurement of water absorption ratio was equivalent to the Shore D hardness of the cured product formed from the composition using QX40. On the other hand, it can be seen that after the measurement of water absorption ratio, the cured product formed from the composition using the curing agent 1 had a higher Shore D hardness and was better than the composition using QX40 and that the Shore D hardness of the cured product formed from the composition using QX40 after the measurement of water absorption ratio was markedly lowered as compared with that before the measurement of water absorption ratio.

[5] Tensile Shear Bond Strength

Example 13, Comparative Example 7

By mixing the components shown in Table 6 at 25° C., an adhesive was prepared. In accordance with JIS-K6850, this adhesive was applied to two galvanized steel plates each having a width of 20 mm and a thickness of 1 mm to bond them so that the length of the bonded area would become 12.5 mm. After 7 days, tensile shear bond strength was measured by a universal testing machine, and the tensile shear bond strength is set forth in Table 6. The unit of each value in compounding is part(s) by mass. A larger value of tensile shear bond strength indicates higher bond strength.

TABLE 6

|  |  | Ex. 13 | Comp. Ex. 7 |
|---|---|---|---|
| Epoxy resin | EP828 | 100 | 100 |
| Curing agent | Curing agent 1 | 70 |  |
|  | QX40 |  | 70 |
| Curing assistant | 3010 | 10 | 10 |
| Tensile shear bond strength (MPa) |  | 10 | 10 |

It can be seen from Table 6 that the tensile shear bond strength of the adhesive of Example 13 prepared by the use of the curing agent containing PE3MB and PE4MB was equivalent to the tensile shear bond strength of the adhesive prepared by the use of QX40.

INDUSTRIAL APPLICABILITY

The thiol compound (P) of the invention has a favorable pot life as an epoxy resin curing agent and has good storage stability. Moreover, use of this thiol compound in combination with a thiol compound (P) which is represented by the formula (1) and has X having at least one hydroxyl group as a substituent decreases extension width of the pot life, and as a result, the pot life can be adjusted to a preferred one.

Furthermore, by preparing the epoxy resin curing agent of the invention under the reduced pressure conditions, odor can be reduced. An epoxy resin cured product obtained by curing this curing agent is excellent also in water resistance and hardness. That is to say, the epoxy resin curing agent of the invention is excellent in workability and reliability, can be used for bonding, sealing, casting, molding, painting and coating materials in transportation equipment, electrical equipment and electronic equipment industries, and is useful as an adhesive or a sealing agent for mounting or fabricating electronic parts requiring rapid curability.

The invention claimed is:

1. An epoxy resin curing agent containing thiol compounds (P) which are represented by the following formula (2):

$$X(-O-CO-CR^1R^2-CR^3R^4-SH)_m \qquad (2)$$

wherein X is an m-valent aliphatic or aromatic residue of at most 20 carbon atoms, which may have a substituent,
$R^1$ and $R^2$ are each independently a hydrogen atom or an alkyl group of 1 to 10 carbon atoms,
$R^3$ and $R^4$ are each independently a hydrogen atom or an alkyl group of 1 to 10 carbon atoms, and at least one of them is an alkyl group of 1 to 10 carbon atoms, and
m is an integer of 2 to 8,
wherein the thiol compounds (P) are a combination of two or more kinds of thiol compounds, and at least one of the thiol compounds (P) has X having at least one hydroxyl group as a substituent and at least one of the thiol compounds (P) has X having no hydroxyl group as a substituent.

2. The epoxy resin curing agent as claimed in claim 1, wherein the thiol compounds (P) are represented by the following formula (3):

$$X(-O-CO-CH_2-CH(CH_3)-SH)_m \qquad (3)$$

wherein X is an m-valent aliphatic or aromatic residue of at most 20 carbon atoms, which may have a substituent, and
m is an integer of 2 to 8.

3. The epoxy resin curing agent as claimed in claim 1, wherein the thiol equivalent of the thiol compounds (P), as defined as a molecular weight based on one thiol group, is in the range of 100 to 500.

4. The epoxy resin curing agent as claimed in claim 1, wherein the hydroxyl group equivalent of the thiol compounds (P), as defined as a molecular weight based on one hydroxyl group, is in the range of 100 to 1000.

5. The epoxy resin curing agent as claimed in claim 1, wherein the thiol compounds (P) include at least one compound selected from the group consisting of ethylene glycol bis(3-mercaptobutyrate), 1,2-propylene glycol bis(3-mercaptobutyrate), 1,3-propylene glycol bis(3-mercaptobutyrate), 1,4-butanediol bis(3-mercaptobutyrate), 2,2-bis(3-(3-mercaptobutyryloxy)-2-hydroxypropyloxyphenyl)propane, glycerol tris(3-mercaptobutyrate), trimethylolpropane tris(3-mercaptobutyrate), trimethylolpropane bis(3-mercaptobutyrate), trimethylolethane bis(3-mercaptobutyrate), pentaerythritol bis(3-mercaptobutyrate), trimethylolethane tris(3-mercaptobutyrate), pentaerythritol tris(3-mercaptobutyrate), tris(3-mercaptobutyryloxyethyl)isocyanurate, a compound wherein two 3-mercaptobutanoic acids have undergone addition to tris(2-hydroxyethyl)isocyanurate, pentaerythritol tetrakis(3-mercaptobutyrate), dipentaerythritol pentakis(3-mercaptobutyrate), bisphenol A dihydroxyethyl ether-3-mercaptobutyrate, 4,4'-(9-fluorenylidene)bis(2-phenoxyethyl(3-mercaptobutyrate)), ethylene glycol bis(3-mercaptovalerate), trimethylolpropane tris(3-mercaptovalerate), trimethylolpropane bis(3-mercaptovalerate), pentaerythritol bis(3-mercaptovalerate), pentaerythritol tris(3-mercaptovalerate), pentaerythritol tetrakis(3-mercaptovalerate), ethylene glycol bis(3-mercaptoisovalerate), trimethylolpropane bis(3-mercaptoisovalerate), pentaerythritol bis(3-mercaptoisovalerate), trimethylolpropane tris(3-mercaptoisovalerate), pentaerythritol tris(3-mercaptoisovalerate) and pentaerythritol tetrakis(3-mercaptoisovalerate).

6. An epoxy resin composition comprising a polyvalent epoxy compound and the epoxy resin curing agent as claimed in claim 1.

7. The epoxy resin composition as claimed in claim 6, wherein the polyvalent epoxy compound is a glycidyl ether compound of a polyhydric alcohol.

8. An adhesive comprising a polyvalent epoxy compound, a curing assistant and the epoxy resin curing agent as claimed in claim 1.

9. The epoxy resin curing agent as claimed in claim 2, wherein the thiol equivalent of the thiol compounds (P), as defined as a molecular weight based on one thiol group, is in the range of 100 to 500.

10. The epoxy resin curing agent as claimed in claim 2, wherein the hydroxyl group equivalent of the thiol compounds (P), as defined as a molecular weight based on one hydroxyl group, is in the range of 100 to 1000.

11. The epoxy resin curing agent as claimed in claim 2, wherein the thiol compounds (P) include at least one compound selected from the group consisting of ethylene glycol bis(3-mercaptobutyrate), 1,2-propylene glycol bis(3-mercaptobutyrate), 1,3-propylene glycol bis(3-mercaptobutyrate), 1,4-butanediol bis(3-mercaptobutyrate), 2,2-bis(3-(3-mercaptobutyryloxy)-2-hydroxypropyloxyphenyl)propane, glycerol tris(3-mercaptobutyrate), trimethylolpropane tris(3-mercaptobutyrate), trimethylolpropane bis(3-mercaptobutyrate), trimethylolethane bis(3-mercaptobutyrate), pentaerythritol bis(3-mercaptobutyrate), trimethylolethane tris(3-mercaptobutyrate), pentaerythritol tris(3-mercaptobutyrate), tris(3-mercaptobutyryloxyethyl)isocyanurate, a compound wherein two 3-mercaptobutanoic acids have undergone addition to tris(2-hydroxyethyl)isocyanurate, pentaerythritol tetrakis(3-mercaptobutyrate), dipentaerythritol pentakis(3-mercaptobutyrate), bisphenol A dihydroxyethyl ether-3-mercaptobutyrate, 4,4'(9-fluorenylidene)bis(2-phenoxyethyl(3-mercaptobutyrate)), ethylene glycol bis(3-mercaptovalerate), trimethylolpropane tris(3-mercaptovalerate), trimethylolpropane bis(3-mercaptovalerate), pentaerythritol bis(3-mercaptovalerate), pentaerythritol tris(3-mercaptovalerate), pentaerythritol tetrakis(3-mercaptovalerate), ethylene glycol bis(3-mercaptoisovalerate), trimethylolpropane bis(3-mercaptoisovalerate), pentaerythritol bis(3-mercaptoisovalerate), trimethylolpropane tris(3-mercaptoisovalerate), pentaerythritol tris(3-mercaptoisovalerate) and pentaerythritol tetrakis(3-mercaptoisovalerate).

12. The epoxy resin curing agent as claimed in claim 3, wherein the thiol compounds (P) include at least one compound selected from the group consisting of ethylene glycol bis(3-mercaptobutyrate), 1,2-propylene glycol bis(3-mercaptobutyrate), 1,3-propylene glycol bis(3-mercaptobutyrate), 1,4-butanediol bis(3-mercaptobutyrate), 2,2-bis(3-(3-mercaptobutyryloxy)-2-hydroxypropyloxyphenyl)propane, glycerol tris(3-mercaptobutyrate), trimethylolpropane tris(3-mercaptobutyrate), trimethylolpropane bis(3-mercaptobutyrate), trimethylolethane bis(3-mercaptobutyrate), pentaerythritol bis(3-mercaptobutyrate), trimethylolethane tris(3-mercaptobutyrate), pentaerythritol tris(3-mercaptobutyrate), tris(3-mercaptobutyryloxyethyl)isocyanurate, a compound wherein two 3-mercaptobutanoic acids have undergone addition to tris(2-hydroxyethyl)isocyanurate, pentaerythritol tetrakis(3-mercaptobutyrate), dipentaerythritol pentakis(3-mercaptobutyrate), bisphenol A dihydroxyethyl ether-3-mercaptobutyrate, 4,4'-(9-fluorenylidene)bis(2-phenoxyethyl(3-mercaptobutyrate)), ethylene glycol bis(3-mercaptovalerate), trimethylolpropane tris(3-mercaptovalerate), trimethylolpropane bis(3-mercaptovalerate), pentaerythritol bis(3-mercaptovalerate), pentaerythritol tris(3-mercaptovalerate), pentaerythritol tetrakis(3-mercaptovalerate), ethylene glycol bis(3-mercaptoisovalerate), trimethylolpropane bis(3-mercaptoisovalerate), pentaerythritol bis(3-mercaptoisovalerate), trimethylolpropane tris(3-mercaptoisovalerate), pentaerythritol tris(3-mercaptoisovalerate) and pentaerythritol tetrakis(3-mercaptoisovalerate).

13. The epoxy resin curing agent as claimed in claim 4, wherein the thiol compounds (P) include at least one compound selected from the group consisting of ethylene glycol bis(3-mercaptobutyrate), 1,2-propylene glycol bis(3-mercaptobutyrate), 1,3-propylene glycol bis(3-mercaptobutyrate), 1,4-butanediol bis(3-mercaptobutyrate), 2,2-bis(3-(3-mercaptobutyryloxy)-2-hydroxypropyloxyphenyl)propane, glycerol tris(3-mercaptobutyrate), trimethylolpropane tris(3-mercaptobutyrate), trimethylolpropane bis(3-mercaptobutyrate), trimethylolethane bis(3-mercaptobutyrate), pentaerythritol bis(3-mercaptobutyrate), trimethylolethane tris(3-mercaptobutyrate), pentaerythritol tris(3-mercaptobutyrate), tris(3-mercaptobutyryloxyethyl)isocyanurate, a compound wherein two 3-mercaptobutanoic acids have undergone addition to tris(2-hydroxyethyl)isocyanurate, pentaerythritol tetrakis(3-mercaptobutyrate), dipentaerythritol pentakis(3-mercaptobutyrate), bisphenol A dihydroxyethyl ether-3-mercaptobutyrate, 4,4'-(9-fluorenylidene)bis(2-phenoxyethyl(3-mercaptobutyrate)), ethylene glycol bis(3-mercaptovalerate), trimethylolpropane tris(3-mercaptovalerate), trimethylolpropane bis(3-mercaptovalerate), pentaerythritol bis(3-mercaptovalerate), pentaerythritol tris(3-mercaptovalerate), pentaerythritol tetrakis(3-mercaptovalerate), ethylene glycol bis(3-mercaptoisovalerate), trimethylolpropane bis(3- mercaptoisovalerate), pentaerythritol bis(3-mercaptoisovalerate), trimethylolpropane tris(3-mercaptoisovalerate), pentaerythritol tris(3-mercaptoisovalerate) and pentaerythritol tetrakis(3-mercaptoisovalerate).

14. The epoxy resin curing agent as claimed in claim 9, wherein the thiol compounds (P) include at least one compound selected from the group consisting of ethylene glycol bis(3-mercaptobutyrate), 1,2-propylene glycol bis(3-mercaptobutyrate), 1,3-propylene glycol bis(3-mercaptobutyrate), 1,4-butanediol bis(3-mercaptobutyrate), 2,2-bis(3-(3-mercaptobutyryloxy)-2-hydroxypropyloxyphenyl)propane, glycerol tris(3-mercaptobutyrate), trimethylolpropane tris(3-mercaptobutyrate), trimethylolpropane bis(3-mercaptobutyrate), trimethylolethane bis(3-mercaptobutyrate), pentaerythritol bis(3-mercaptobutyrate), trimethylolethane tris(3-mercaptobutyrate), pentaerythritol tris(3-mercaptobutyrate), tris(3-mercaptobutyryloxyethyl)isocyanurate, a compound wherein two 3-mercaptobutanoic acids have undergone addition to tris(2-hydroxyethyl)isocyanurate, pentaerythritol tetrakis(3-mercaptobutyrate), dipentaerythritol pentakis(3-mercaptobutyrate), bisphenol A dihydroxyethyl ether-3-mercaptobutyrate, 4,4'-(9-fluorenylidene)bis(2-phenoxyethyl(3-mercaptobutyrate)), ethylene glycol bis(3-mercaptovalerate), trimethylolpropane tris(3-mercaptovalerate), trimethylolpropane bis(3-mercaptovalerate), pentaerythritol bis(3-mercaptovalerate), pentaerythritol tris(3-mercaptovalerate), pentaerythritol tetrakis(3-mercaptovalerate), ethylene glycol bis(3-mercaptoisovalerate), trimethylolpropane bis(3-mercaptoisovalerate), pentaerythritol bis(3-mercaptoisovalerate), trimethylolpropane tris(3-mercaptoisovalerate), pentaerythritol tris(3-mercaptoisovalerate) and pentaerythritol tetrakis(3-mercaptoisovalerate).

15. The epoxy resin curing agent as claimed in claim 10, wherein the thiol compounds (P) include at least one compound selected from the group consisting of ethylene glycol bis(3-mercaptobutyrate), 1,2-propylene glycol bis(3-mercaptobutyrate), 1,3-propylene glycol bis(3-mercaptobutyrate), 1,4-butanediol bis(3-mercaptobutyrate), 2,2-bis(3-(3-mercaptobutyryloxy)-2-hydroxypropyloxyphenyl)propane, glycerol tris(3-mercaptobutyrate), trimethylolpropane tris(3-mercaptobutyrate), trimethylolpropane bis(3-mercaptobutyrate), trimethylolethane bis(3-mercaptobutyrate), pentaerythritol bis(3-mercaptobutyrate), trimethylolethane tris(3-mercaptobutyrate), pentaerythritol tris(3-mercaptobutyrate), tris(3-mercaptobutyryloxyethyl)isocyanurate, a compound wherein two 3-mercaptobutanoic acids have undergone addition to tris(2-hydroxyethyl)isocyanurate, pentaerythritol tetrakis(3-mercaptobutyrate), dipentaerythritol pentakis(3-mercaptobutyrate), bisphenol A dihydroxyethyl ether-3-mercaptobutyrate, 4,4'-(9-fluorenylidene)bis(2-phenoxyethyl(3-mercaptobutyrate)), ethylene glycol bis(3-mercaptovalerate), trimethylolpropane tris(3-mercaptovalerate), trimethylolpropane bis(3-mercaptovalerate), pentaerythritol bis(3-mercaptovalerate), pentaerythritol tris(3-mercaptovalerate), pentaerythritol tetrakis(3-mercaptovalerate), ethylene glycol bis(3-mercaptoisovalerate), trimethylolpropane bis(3-mercaptoisovalerate), pentaerythritol bis(3-mercaptoisovalerate), trimethylolpropane tris(3-mercaptoisovalerate), pentaerythritol tris(3-mercaptoisovalerate) and pentaerythritol tetrakis(3-mercaptoisovalerate).

16. An epoxy resin composition comprising a polyvalent epoxy compound and the epoxy resin curing agent as claimed in claim 2.

17. An epoxy resin composition comprising a polyvalent epoxy compound and the epoxy resin curing agent as claimed in claim 3.

18. An epoxy resin composition comprising a polyvalent epoxy compound and the epoxy resin curing agent as claimed in claim 4.

19. An epoxy resin composition comprising a polyvalent epoxy compound and the epoxy resin curing agent as claimed in claim 9.

20. An epoxy resin composition comprising a polyvalent epoxy compound and the epoxy resin curing agent as claimed in claim 10.

* * * * *